(12) United States Patent
Viljoen et al.

(10) Patent No.: US 12,035,949 B2
(45) Date of Patent: *Jul. 16, 2024

(54) PERCUTANEOUS TRANSVERSE CONNECTOR SYSTEM

(71) Applicant: The University of Iowa Research Foundation, Iowa City, IA (US)

(72) Inventors: Stephanus V. Viljoen, North Liberty, IA (US); Andrew Grossbach, Iowa City, IA (US)

(73) Assignee: THE UNIVERSITY OF IOWA RESEARCH FOUNDATION, Iowa City, IA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/079,551

(22) Filed: Dec. 12, 2022

(65) Prior Publication Data

US 2023/0106758 A1 Apr. 6, 2023

Related U.S. Application Data

(60) Continuation of application No. 16/589,911, filed on Oct. 1, 2019, now abandoned, which is a division of (Continued)

(51) Int. Cl.
 *A61B 17/70* (2006.01)
(52) U.S. Cl.
 CPC ...... *A61B 17/7089* (2013.01); *A61B 17/7043* (2013.01); *A61B 17/7052* (2013.01);
(Continued)

(58) Field of Classification Search
 CPC ............ A61B 17/7052; A61B 17/7047; A61B 17/7056
 See application file for complete search history.

(56) References Cited

U.S. PATENT DOCUMENTS

| 5,330,473 A | 7/1994 | Howland |
| 6,530,929 B1 | 3/2003 | Justis et al. |

(Continued)

FOREIGN PATENT DOCUMENTS

| JP | 2003-511190 | 3/2003 |
| WO | 94/10928 | 5/1994 |

*Primary Examiner* — Julianna N Harvey
(74) *Attorney, Agent, or Firm* — Peacock Law P.C.; Janeen Vilven (57) ABSTRACT

A system and method for stabilizing a spine of an animal subject involving a transverse rod installation instrument assembly for inserting a transverse rod on the spine of a subject percutaneously comprising: a first rod clamp extender mounted on a ipsilateral rod clamp and a second rod clamp extender mounted on a contralateral rod clamp wherein the ipsilateral rod clamp and the contralateral rod clamp are secured to a vertebra at the ipsilateral and contralateral pedicle; and a pivoting installation instrument pivotably mounted to the first rod clamp extender and the second rod clamp extender to pass a transverse rod percutaneously through a head portion of the ipsilateral side rod clamp and to the head portion of the contralateral rod clamp after passing through a spinous process of the vertebra through pivot axis "A" such that the transverse rod is secured at the head portion of the ipsilateral rod clamp and the head portion of the contralateral rod clamp.

3 Claims, 7 Drawing Sheets

Related U.S. Application Data application No. 15/141,745, filed on Apr. 28, 2016, now Pat. No. 10,426,528, which is a continuation of application No. PCT/US2014/063152, filed on Oct. 30, 2014.

(60) Provisional application No. 61/898,332, filed on Oct. 31, 2013.

(52) U.S. Cl.
CPC ...... *A61B 17/7076* (2013.01); *A61B 17/7083* (2013.01); *A61B 17/7085* (2013.01)

(56) References Cited

U.S. PATENT DOCUMENTS

| | | | |
|---|---|---|---|
| 6,740,089 B2 | 5/2004 | Haider | |
| 6,916,319 B2 * | 7/2005 | Munting | A61B 17/7043 606/250 |
| 7,794,479 B2 | 9/2010 | Aferzon | |
| 7,879,039 B2 | 2/2011 | Perez-Cruet et al. | |
| 7,993,342 B2 | 8/2011 | Malandain et al. | |
| 8,043,345 B2 | 10/2011 | Carl et al. | |
| 8,070,751 B2 | 12/2011 | Justis et al. | |
| 8,142,437 B2 | 3/2012 | Mclean et al. | |
| 8,197,522 B2 | 6/2012 | Park et al. | |
| 8,414,620 B2 | 4/2013 | Sherman et al. | |
| 10,426,528 B2 * | 10/2019 | Viljoen | A61B 17/7052 |
| 2002/0161368 A1 | 10/2002 | Foley | |
| 2005/0043740 A1 | 2/2005 | Haid, Jr. et al. | |
| 2008/0051782 A1 | 2/2008 | Wu | |
| 2008/0249531 A1 * | 10/2008 | Patterson | A61B 17/7089 606/300 |
| 2009/0187217 A1 | 7/2009 | Weiman et al. | |
| 2010/0160981 A1 | 6/2010 | Butler et al. | |
| 2011/0087293 A1 | 4/2011 | Ferreira et al. | |
| 2011/0301647 A1 | 12/2011 | Hua | |
| 2013/0018419 A1 | 1/2013 | Rezach et al. | |
| 2013/0030467 A1 | 1/2013 | Karas et al. | |
| 2013/0072987 A1 | 3/2013 | Justis et al. | |
| 2013/0096635 A1 * | 4/2013 | Wall | A61B 90/92 606/305 |
| 2013/0110184 A1 | 5/2013 | Wing et al. | |
| 2013/0150890 A1 | 6/2013 | Mclean et al. | |
| 2014/0135839 A1 * | 5/2014 | Frankel | A61B 17/00234 606/279 |
| 2016/0242827 A1 | 8/2016 | Viljoen et al. | |
| 2020/0038073 A1 | 2/2020 | Viljoen et al. | |

\* cited by examiner

PERCUTANEOUS TRANSVERSE CONNECTOR SYSTEM

CROSS-REFERENCE TO RELATED APPLICATIONS

This application is a continuation of U.S. patent application Ser. No. 16/589,911, entitled "Percutaneous Transverse Connector System", filed on Oct. 1, 2019, which is a division of U.S. patent application Ser. No. 15/141,745, entitled "Percutaneous Transverse Connector System", filed on Apr. 28, 2016, and issued on Oct. 1, 2019 as U.S. Pat. No. 10,426,528, which is a continuation of International Application PCT/US14/63152, entitled "Percutaneous Transverse Connector System", filed Oct. 30, 2014, which claims priority to and the benefit of the filing of U.S. Provisional Patent Application No. 61/898,332, entitled "Percutaneous Transverse Connector System", filed on Oct. 31, 2013, and the specification and claims thereof are incorporated herein by reference.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

COPYRIGHTED MATERIAL

Not Applicable.

BACKGROUND

The system and method of this invention relates to an implantable spinal fixation system for the surgical treatment of spinal disorders and apparatus for implantation.

Spinal column disorders such as scoliosis, kyphosis, lordosis, spondylolisthesis, ruptured, broken, fractured or slipped discs are treated with spinal fixation. Spinal fixation uses surgical implants or constructs which mechanically immobilize the treated area of the spine with the goal of causing the fusion of the treated vertebrae. One type of spinal fixation utilizes a pair of longitudinal rods that run parallel or longitudinally along the spine and are affixed to pedicles of the appropriate vertebrae or to the sacrum and act as anchor points for the longitudinal rods. Bone screws are generally placed two per vertebrae with one at each pedicle on either side of the spinous process of the vertebrae. Clamp assemblies join the spine rods to the screws. When a pair of transverse rod/connectors are fastened in parallel on either side of the spinous process, the assembly can be significantly strengthened. However, the instrumentation with transverse rods described requires open surgery and a large incision. In doing so, the skin and tissue surrounding the surgical site must be cut, removed and or repositioned in order for the surgeon to access the location where the stabilization device is to be installed. This type of invasive surgery leads to risk of long recovery time, disruption of muscle, trauma damage and scarring to the tissue.

In recent years minimally invasive spinal (MIS) procedures have become more common. The advantages of MIS procedures compared with open surgery are less pain, faster recovery, less intra-operative blood loss, and generally greater patient satisfaction. With the advent of innovative devices and techniques, physicians now routinely perform MIS procedures that traditionally would require open surgery. One of the shortcomings of MIS procedure/surgery is the inability to place a transverse connector through a percutaneous route. Transverse connectors are used during spinal instrumentation procedures to add rigidity to the overall construct offered by longitudinal rods alone. Transverse rods add stability during axial rotation (twisting) and lateral bending (side to side bending) of the spine. During open procedures the placement of transverse connectors are straight forward but require muscle dissection as well as other downsides mentioned herein.

Minimally invasive surgery wherein a long incision through a muscle group such as those along the spine to expose multiple levels of vertebrae is not required. Minimally invasive surgery may be achieved with percutaneous minimally invasive spinal procedures where minimal if any muscle dissection is required. Currently minimally invasive surgery is not available to insert transverse rods into the spine, for example, to add rigidity to an instrumentation construct consisting of pedicle screws and longitudinal rods involving multiple levels of vertebrae.

BRIEF DESCRIPTION OF THE INVENTION

One embodiment of the present invention provides a transverse rod installation instrument assembly for inserting a transverse rod on the spine of a subject percutaneously. A first rod clamp extender is mounted on an ipsilateral rod clamp and a second rod clamp extender is mounted on a contralateral rod clamp wherein the ipsilateral rod clamp and the contralateral rod clamp are secured to a vertebra at the ipsilateral and contralateral pedicle. A pivoting installation instrument is pivotably mounted to the first rod clamp extender and the second rod clamp extender to pass a transverse rod percutaneously through a head portion of the ipsilateral side rod clamp and to the head portion of the contralateral rod clamp after passing through a spinous process of the vertebra through pivot axis "A" path such that the transverse rod is secured at the head portion of the ipsilateral rod clamp and the head portion of the contralateral rod clamp. Further, the first rod clamp extender has a cylinder with a pair of opposing arms that extends superior to the cylinder wherein at the bottom of the cylinder is a docking ring for engaging with the bolts on a pair of opposing wings of the ipsilateral rod clamp assembly when the cylinder of the first rod clamp extender is positioned over the pair of opposing wings. The pair of opposing arms on the first rod clamp extender includes a hole in each arm of the pair wherein the hole in each arm of the pair of opposing arms aligns. The second rod clamp extender has a cylinder with a pair of opposing arms that extends superior to the cylinder wherein at the bottom of the cylinder is a docking ring for engaging with the bolts on a pair of opposing wings of the contralateral rod clamp assembly when the cylinder of the second rod clamp extender is positioned over the pair of opposing wings. The docking ring has an internal grove for securing the bolt on the side of the wing of the rod clamp assembly when the rod clamp assembly is in use to stabilize the extender onto the rod clamp assembly. The pair of opposing arms on the second rod clamp extender includes a hole in each arm of the pair wherein the hole in each arm of the pair aligns. The first rod clamp extender and the second rod clamp extender are secured together with a bolt that fits through each hole in each arm of the pair of opposing arms of the first rod clamp extender and each hole in each arm of the pair of opposing arms of the second rod clamp extender such that the bolt passes first through an arm of a first rod clamp extender and then through an arm of the second rod clamp extender before passing through the opposing arm of the first rod clamp extender and then the opposing arm of the second rod clamp extender. The pivoting installation instrument pivotably mounted to the first rod clamp extender and the second rod clamp extender is secured to the first rod clamp extender and the second rod clamp extender via the bolt.

Another embodiment of the present invention provides for an orthopedic clamp system for use with a rod for immobilizing bone comprising a rod clamp assembly having a clamp with an upper surface and a lower surface and a rod receiving section positioned superior to the clamp the rod receiving section having a pair of opposing wings that extend from the rod receiving section. The clamp includes a tightening screw through its upper surface for securing the clamp to a longitudinal rod immobilized to the bone and a polyaxial head that is positioned between the rod receiving section and the clamp. The polyaxial head allows for freedom of movement when positioning a transverse rod passer in the rod receiving section. The rod receiving section is threaded to mate with a set screw to tighten a transverse rod positioned in the rod receiving section. The pair of opposing wings include a bolt on an outer surface of the pair of opposing wings used to secure a docking ring of a rod clamp extender when the rod clamp extender is positioned over the pair of opposing wings. The pair of opposing wings create an open space along the length "L" of the rod clamp assembly which space permits a transverse rod receiving section to be observed from above. The wings above the rod receiving section are releaseably attached to the rod receiving section.

Another embodiment of the present invention provides for a method for inserting a transverse spinal rod into a patient comprising attaching a first rod clamp assembly onto a first longitudinal rod that is secured to a first vertebrae having a first side of a spinous process of the patient wherein the first rod clamp assembly is introduced to the longitudinal rod through a first minimally invasive incision on the back of the patient at the level of the first vertebrae. A second rod clamp is attached to the assembly onto a second longitudinal rod that is secured to the first vertebrae on a second side of the spinous process of the patient wherein the second rod clamp assembly is introduced to the longitudinal rod through a second minimally invasive incision on the back of the patient at the level of the first vertebrae. A first rod clamp extender is placed onto a pair of opposing wings of the first rod clamp assembly. A clamp of the first rod clamp assembly is secured to the first longitudinal rod with a screw on the upper surface of the clamp of the first rod clamp assembly. A second rod clamp extender is secured onto a pair of opposing wing of the second rod clamp assembly. A clamp of the second rod clamp assembly is secured to the second longitudinal rod with a screw on the upper surface of the clamp of the second rod clamp assembly. An extracorporeal portion of the first rod clamp extender is secured to an extracorporeal portion of the second rod clamp extender via a transverse rod passer pivotably mounted to the first rod clamp extender and the second rod clamp extender about a pivot axis "A" whose pivot axis passes through the head of the first rod clamp assembly, the spinous process, and the head of the second rod clamp assembly. A transverse rod opening is created in the spinous process by piercing the spinous process with an awl that is directed to the spinous process via the transverse rod passer as the transverse rod passer is moved through pivot axis "A" path percutaneously. The transverse rod connector is inserted into the head of the second rod clamp assembly after passing through the spinous process and through the head of the first rod clamp assembly via the transverse rod connector guiding the transverse rod through pivot axis "A" path. The transverse rod is secured to the first rod clamp assembly.

Further still, the transverse rod is connected to a handle with a flexible section that is removable from the transverse rod for allowing the transverse rod to be positioned in a guide tube of the transverse rod passer. An awl for creating an opening in the spinous process includes a handle having a flexible shaft and a sharp tip portion that is inserted through the guide tube of the transverse rod passer. The first rod clamp assembly and the second rod clamp assembly is disconnected from the transverse rod passer. The screw on the upper surface of the clamp of the first rod clamp assembly is tightened with a screw driver inserted percutaneously. The pair of opposing wings of the first rod clamp assembly is detached from the head portion leaving the head portion secured to the transverse rod.

Further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings in the attachment, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

As used herein "a" or "an" means one or more.

One aspect of one embodiment of a present invention provides for a system and method for placement of a transverse connector on the spine of an animal subject (e.g. human) wherein minimal if any muscle dissection is required.

A set of innovative instruments and method of using the same that allow precise placement of a transverse rod across the vertebrae to a transverse rod connector through a percutaneous route.

According to one embodiment of the present invention a method for spinal fusion of adjacent vertebral bodies is provided wherein an installation instrument for guiding a transverse rod to connect with a rod clamp through a minimally invasive incision is discussed. The method further provides that the transverse rod is passed through the head of an ipsilateral rod clamp and inserted through spinous process before connecting with the head of a contralateral rod clamp.

An aspect of the present invention provides a transverse rod installation instrument for transcutaneous placement of a transverse rod wherein the installation instrument is mounted to rod clamp extensions whose position is secured in an animal subject.

One aspect of one embodiment of the present invention is a minimally invasive method to stabilize bony structures.

One aspect provides for a method to connect two (2) or more rod clamps with a connecting element.

A method to attach a transverse rod inserter on an installation instrument to the extensions and guiding the transverse rod into a desired position relative to the rod clamps.

A fixed geometric relationship to guide the transverse rod into a position proximate to the rod clamps.

According to one embodiment of the present invention an installation instrument is mounted to the rod clamp extension element in spatial relation to the anchors about a pivot point. The instrument is rotated about the pivot point to guide the transverse rod to the desired location.

According to another embodiment of the present invention an installation instrument assembly is provided having an ispilateral rod clamp extension designed to slide onto the wings of an ipsilateral rod clamp and a contralateral rod clamp extension designed to slide onto the wings of a contralateral rod clamp. The rod clamp extensions each have an arm with a hole at the end of the arm through which the two rod clamp extensions are secured together. The installation instrument mounts to the ipsilateral and contralateral rod clamp extension arms when the rod clamp extensions are mounted to rod clamps positioned on either side of the spinous process of a vertebra. In this position, the two arms will overlap slightly when the rod clamp extensions are properly positioned on the rod clamps to allow the holes at the end of each arm to overlap. The installation assembly is held together with a fastener that passes through all four holes of the arms including the holes of the arms and the holes at the attachment ends of the installation instrument which sandwich the two holes of the arms to connect the installation instrument assembly together. The rod clamps 101 to which the rod clamp extension 104 are mounted are positioned on either side of spinous process and the rod clamps are secured to a pedicle of a vertebra structure with pedicle screws (see 107 of FIG. 6). The installation instrument is pivotable about a pivot axis that is formed by a line that runs through the holes of the side arms and holes of the attachment ends when assembled. The installation instrument is moveable with respect to the rod clamps to position a transverse brace through the spinous process of the vertebra and secure the ends of the transverse rod to the head of the ipsilateral and contralateral rod clamps.

Figure 1A:
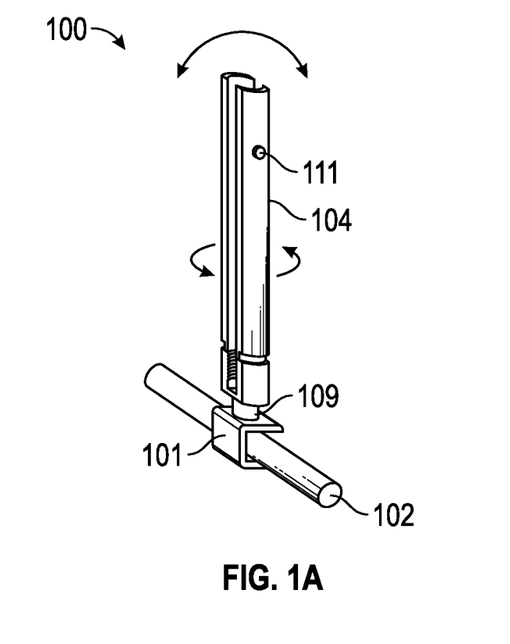
FIG. 1A-C is an illustration of a rod clamp and rod clamp assembly according to one embodiment of the present invention from different view.
Figure 1B:
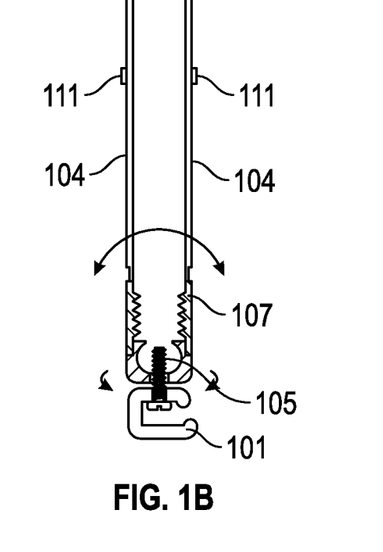
Figure 1C:
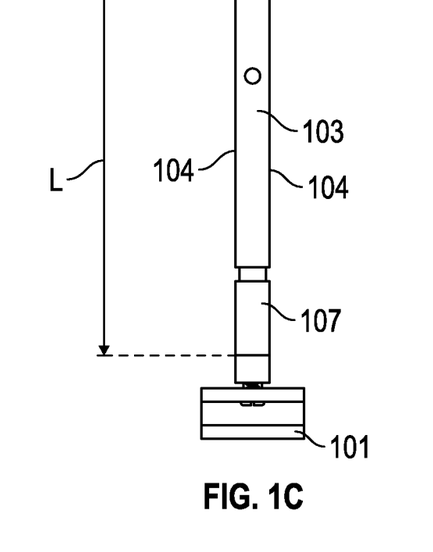

Referring now to FIG. 1A rod clamp assembly 100 having a pair of opposing wings 104 that extend from clamp 101 includes a tightening screw 105 which locks the clamp 101 to the longitudinal rod 102 (not shown). There is a polyaxial head 109 which allows for freedom of movement when positioning the rod passer. Referring now to FIG. 1B, a tightening screw 105 sits in the superior portion of the clamp 101 and acts to close down on the longitudinal rod on the medial side of the rod but can secure the rod on the lateral side of the rod as well. As shown by the arrows at the wings, the poilyaxial head also allows for rotation. Bolts 111 are positioned on the side of the wings and are used to secure the extenders (not shown) when the extenders are positioned over the wings. Referring now to FIG. 1C, the clamp 101 is secured to a longitudinal rod 102. The longitudinal rod 102 is secured to a bony structure such as a vertebra with a pedicle screw inserted into a pedicle of the vertebra. The longitudinal rod 102 is positioned in the clamp 101. Once pedicle screws and longitudinal rods are placed, a site is identified on the rod clamp 100 where the transverse connector will be connected, for example at head 107 of rod clamp assembly 100. The head 107 has threads and below the threads a transverse rod trough which is located superior to the clamp 101. FIG. 1C is a side view of the rod clamp and wings. The wings 104 create a space 103 along the length "L" of the rod clamp as illustrated. A portion of the wings of the rod clamp assembly is located extracorporeal. An empty portion at the head 107 of rod clamp assembly is identified where the transverse connector will be attached and secured with set screws. The set screws are introduced through the distal opening of the rod clamp assembly.

Facial openings are made is the skin and muscle and a standard nasal speculum is used to visualize the rod clamp 100 and longitudinal rod 102.

Figure 2:
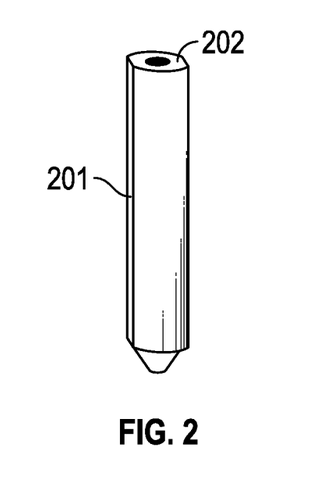
FIG. 2 is a stabilizing tower to slide over wings of a rod clamp according to one embodiment of the present invention.
Figure 5:
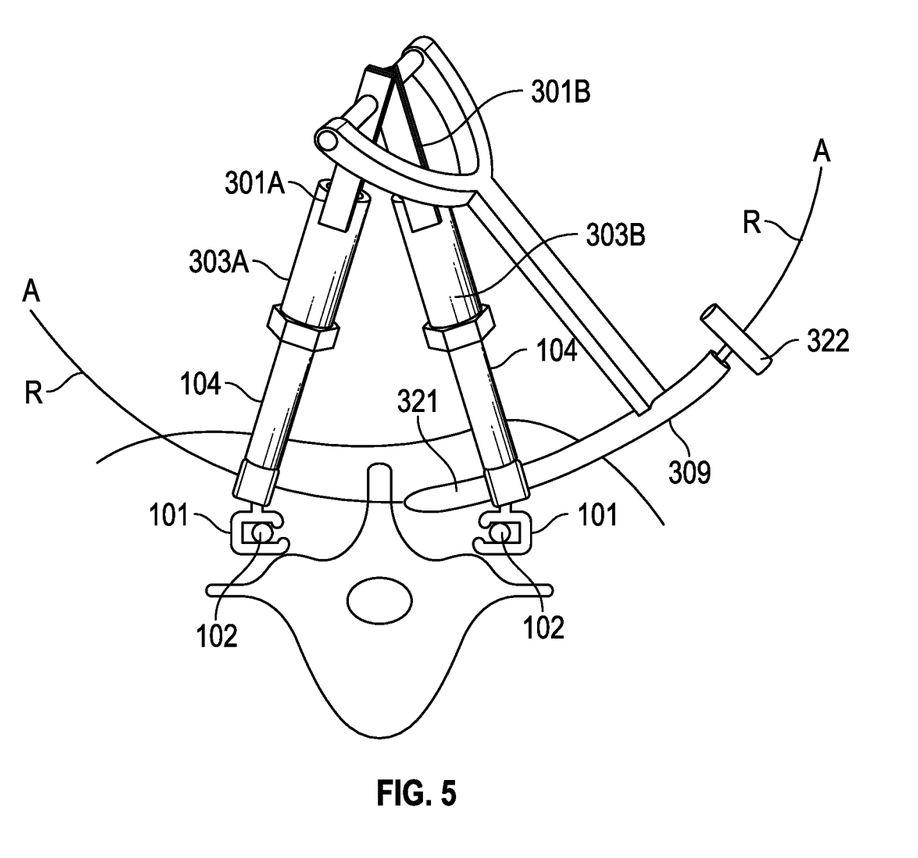
FIG. 5 illustrates a transverse rod passer assembly in association with a spinous process of a vertebra according to one embodiment of the present invention.

Referring now to FIG. 2, a stabilizing tower 201 is placed on the wings 104 of the rod clamp assembly 100 and passes down the rod clamp wings 104. Opening 202 in stabilizing tower 201 is used to insert screw driver for tightening screw 105 of FIG. 1B. Once the clamp is seated on the longitudinal rod for example, the rod clamp sits as deep as possible against the longitudinal rod. The tightening screw 105 on the rod clamp 101 is tightened to prevent the rod clamp 101 from becoming disengaged from the longitudinal rod 102. In the case of a spinal fusion there would be two rod clamps with a first rod clamp secured on a left pedicle of vertebra V and a second rod clamp secured on a right pedicle of vertebra V as is shown in FIG. 5.

Figure 3A:
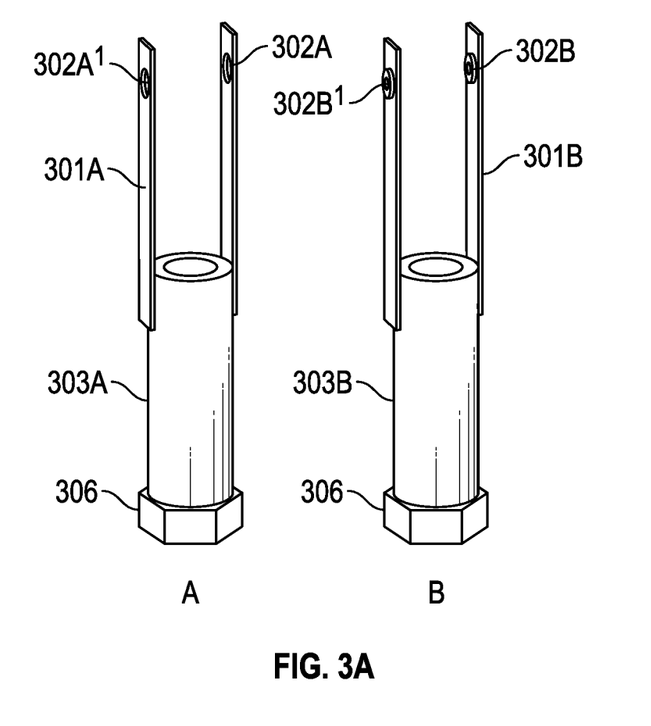
FIG. 3A-G illustrates a transverse rod passer system according to one embodiment of the present invention.
Figure 3B:
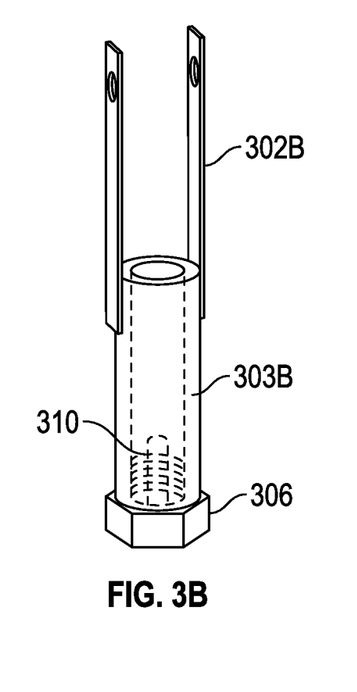
Figure 3C:
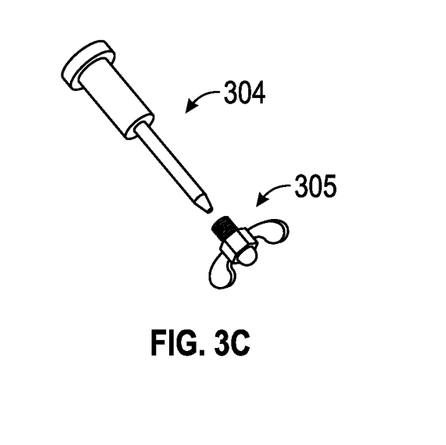
Figure 3D:
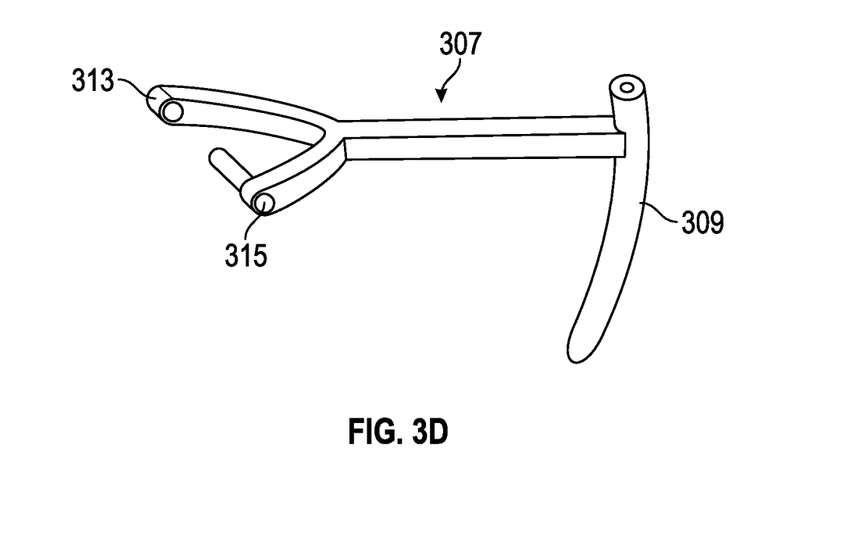
Figure 3E:
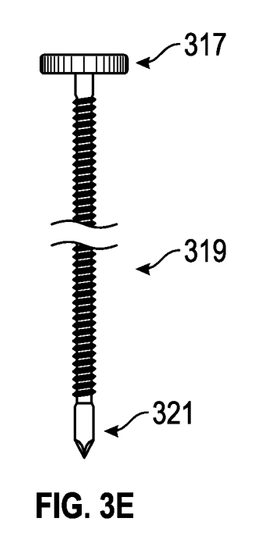
Figure 3F:
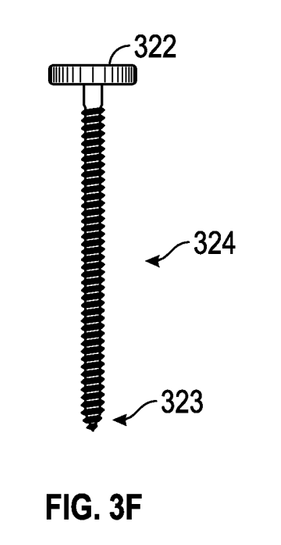
Figure 3G:
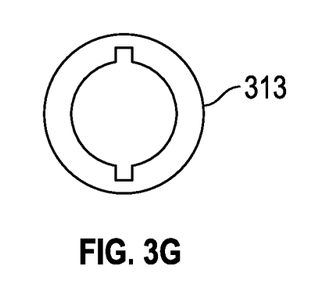

The stabilizing tower is removed from the rod clamp wings. Referring now to FIG. 3A-3G, rod clamp extender/extension 303A having arm 301A with a hole 302A is placed over the wings of a rod clamp assembly 100. Rod clamp extender/extension cyclinder 303B having arm 301B with a hole 302B is placed over the wings of a second rod clamp attached to a different part of the bony structure. Hole 302A is aligned with hole 302B having a bolt that fits in hole 302A while hole $302A^1$ is aligned with hole $302B^1$ having a bolt that fits in hole $302A^1$ and also with attachment end 315 of FIG. 3D and attachment end 313 of FIG. 3D of installation instrument 307 of FIG. 3D such that rod clamp extension 303A, rod clamp extension cyclinder 303B and installment instrument 307 can be secured together by nut 305 at the end of rod 304 of FIG. 3C as is illustrated for the assembly in FIG. 4. An awl 329 of FIG. 3E having a handle 317, a flexible shaft (for example a spring) 319 and a tip portion 321 is inserted through the guide tube 309 of instrument 307 as illustrated in FIG. 3D. The flexible shaft permits the shaft 319 of the awl to flex during insertion in guide tube 309. FIG. 3B identifies the interior of the extender of either 303A or 303B. There is a docking ring 306 for locking the extender onto the bolt 111 of wing 104 when the assembly is in use and the rod is passed through the spinous process. An internal grove 310 secures the bolt 111 to stabilize the extender onto the wing of the rod clamp. FIG. 3F illustrate a transverse rod connected to a handle with a flexible section. The handle and flexible section are removeable from the transverse rod. The portion of 324 that is flexible for allowing the transverse rod to be positioned in guide tube 309. FIG. 3G illustrates a cross sectional view 316 of the extenders in position over the rod clamp wings. The groove 317 at the bottom of the extenders slide over the bolts 111. Once the extenders are securely seated, the docking ring 306 locks the extender onto the rod clamp wings.

Figure 4:
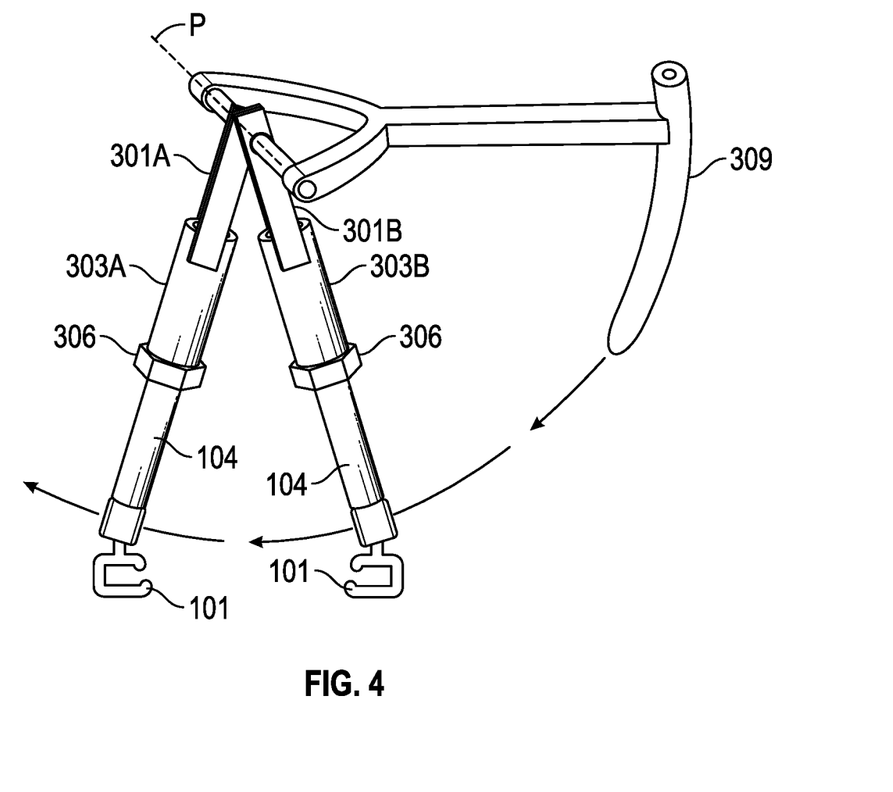
FIG. 4 illustrates a transverse rod installment instrument assembly according to one embodiment of the present invention.

Referring now to FIG. 4, the installation instrument assembly 307 attached to the arms of rod clamp extender is illustrated. The pivot Axis "P" about which the installation instrument pivots is illustrated. The arms 301A and 301B join and may be connected to attachment end 315 and attachment end 313 with connector of FIG. 3C. Alternative installment instrument 307 can be used with end 305 securing section 304 in place.

A skin and facial incision is made for when the awl 329 enters the skin on the Ipsilateral side of the body and the guide tube 309 is advanced until the spinous process is encountered. Referring now to FIG. 5, with firm pressure the awl 329 positioned in guide tube 309 is advanced through the spinous process along arc A on radius R. Visual confirmation through the contralateral rod clamp will confirm that the awl has passed through the spinous process. The guide tube 309 sits in the tranverse rod trough of 107 which is superior to 101 but leaves adequate space at the bottom for the awl 329 to pass through.

Figure 6:
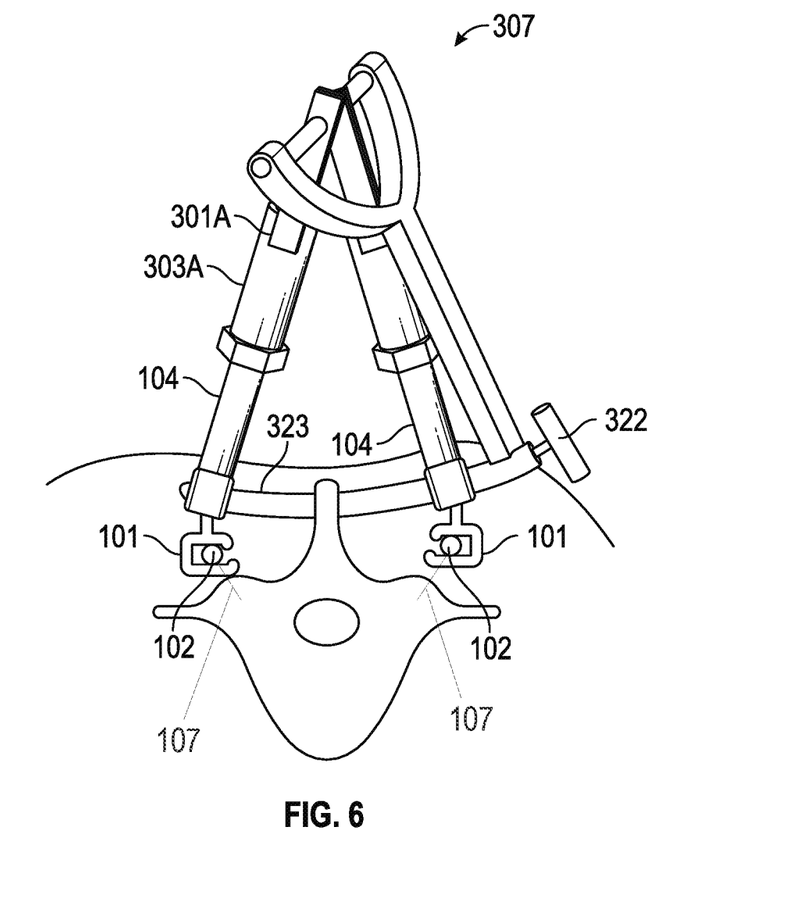
FIG. 6 illustrates a transverse rod through the spinous process of a vertebra in association with the transverse rod passer assembly according to one embodiment of the present invention.

Referring now to FIG. 6, the guide tube 309 follows the same trajectory as the awl is then swung out, the awl is removed and a permanent transverse rod 324 of the appropriate length (confirmed on fluoroscopy) is inserted in the guide tube 309 of the traverse rod passer. The guide tube 309 of the transverse rod passer is again advanced through arc A over radius R until the transverse rod 323 is appropriately seated in the head portion 107 of the rod clamps 101. The installation instrument is removed. The rod clamp extension is removed and wings 104 are broken off above section 107 leaving behind the transverse rod anchor 703 located superior to the clamp 101 with the transverse rod and the longitudinal rod in position secured to the bony structures of the pedicle and the spinous process.

Figure 7:
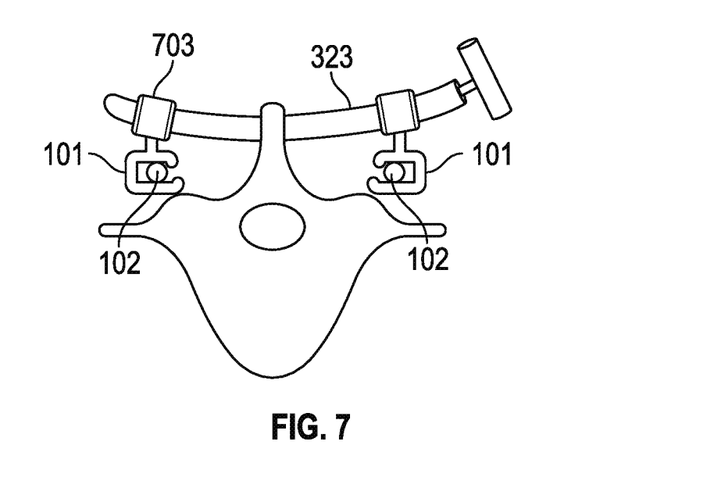
FIG. 7 illustrates a transverse rod associated with rod clamps and bony structure of a vertebra according to one embodiment of the present invention.

Referring now to FIG. 7, transverse rod anchor 703 secured to the transverse rod 323 via set screws (not shown) with clamp 101 secured to longitudinal rod 102 with longitudinal rod 102 secured to the vertebrae by pedicle screws (not shown) is illustrated.

Although the invention has been described in detail with particular reference to these preferred embodiments, other embodiments can achieve the same results. Variations and modifications of the present invention will be obvious to those skilled in the art and it is intended to cover in the appended claims all such modifications and equivalents. The entire disclosures of all references, applications, patents, and publications cited above are hereby incorporated by reference

What is claimed is:

1. A method for inserting a transverse spinal rod on a spine of a subject comprising:
   attaching an ipsilateral rod clamp to an ipsilateral pedicle of a vertebra;
   attaching a contralateral rod clamp to a contralateral pedicle of the vertebra;
   mounting a first rod clamp extender on the ipsilateral rod clamp and mounting a second rod clamp extender on the contralateral rod clamp;
   passing a transverse rod percutaneously through a head portion of the ipsilateral rod clamp and to a head portion of the contralateral rod clamp after passing through a spinous process of the vertebra along arc (A) on radius (R) such that the transverse rod is secured at the head portion of the ipsilateral rod clamp and the head portion of the contralateral rod clamp, wherein— each head portion is superior to a longitudinal rod receiving section having an upper surface and a lower surface and having a tightening screw through its upper surface for securing the longitudinal rod receiving section to a longitudinal rod when positioned therein, and positioned between a transverse rod receiving section and the longitudinal rod receiving section is a polyaxial head to allow for freedom of movement when positioning the transverse rod in the transverse rod receiving section.

2. The method of claim 1 wherein the transverse rod is connected to a handle with a flexible section that is removable from the transverse rod for allowing the transverse rod to be positioned in a guide tube of a transverse rod passer.

3. The method of claim 1 wherein the tightening screw is tightened for securing a longitudinal rod in the longitudinal rod receiving section.

* * * * *